(12) United States Patent
Xiong et al.

(10) Patent No.: US 11,174,270 B2
(45) Date of Patent: Nov. 16, 2021

(54) CRYSTAL FORM OF 3,4-DIHYDROTHIENO[3,2-D]PYRIMIDINE COMPOUND AND PREPARATION METHOD THEREOF

(71) Applicant: PHAENO THERAPEUTICS CO., LTD., Zhejiang (CN)

(72) Inventors: Jian Xiong, Shanghai (CN); Jingjing Wang, Shanghai (CN); Boyu Hu, Shanghai (CN); Haizhong Tan, Shanghai (CN); Kevin X. Chen, Shanghai (CN); Jian Li, Shanghai (CN); Shuhui Chen, Shanghai (CN)

(73) Assignee: Phaeno Therapeutics Co., Ltd., Zhejiang (CN)

( * ) Notice: Subject to any disclaimer, the term of this patent is extended or adjusted under 35 U.S.C. 154(b) by 0 days.

(21) Appl. No.: 16/968,206

(22) PCT Filed: Jan. 29, 2019

(86) PCT No.: PCT/CN2019/073700
§ 371 (c)(1),
(2) Date: Aug. 7, 2020

(87) PCT Pub. No.: WO2019/154192
PCT Pub. Date: Aug. 15, 2019

(65) Prior Publication Data
US 2021/0024538 A1    Jan. 28, 2021

(30) Foreign Application Priority Data

Feb. 8, 2018  (CN) .......................... 201810130625.8

(51) Int. Cl.
*C07D 495/04*    (2006.01)

(52) U.S. Cl.
CPC ........ *C07D 495/04* (2013.01); *C07B 2200/13* (2013.01)

(58) Field of Classification Search
CPC .......................... C07D 495/04; C07B 2200/13
See application file for complete search history.

(56) References Cited

U.S. PATENT DOCUMENTS

| | | | |
|---|---|---|---|
| 7,196,086 B2 | 3/2007 | Wunberg et al. | |
| 7,662,822 B2 | 2/2010 | Wunberg et al. | |
| 2019/0202838 A1* | 7/2019 | Xiong | ..................... A61P 31/22 |

FOREIGN PATENT DOCUMENTS

| | | |
|---|---|---|
| CN | 1784390 A | 6/2006 |
| CN | 1980925 A | 6/2007 |
| WO | 2016/109360 A1 | 7/2016 |
| WO | 2018/028556 A1 | 2/2018 |

* cited by examiner

*Primary Examiner* — Timothy R Rozof
(74) *Attorney, Agent, or Firm* — McDermott Will & Emery LLP

(57) ABSTRACT

A crystal form A of a 3,4-dihydrothieno[3,2-d]pyrimidine compound (1), a preparation method therefor and an application thereof in the preparation of an anti-human cytomegalovirus (HCMV) drug.

14 Claims, 2 Drawing Sheets

FIG. 3

CRYSTAL FORM OF 3,4-DIHYDROTHIENO[3,2-D]PYRIMIDINE COMPOUND AND PREPARATION METHOD THEREOF

CROSS-REFERENCE TO RELATED APPLICATIONS

This application is a national state filing under 35 U.S.C. § 371 of International Application No. PCT/CN2019/073700, filed on Jan. 29, 2019, which claims the priority of CN201810130625.8, filed on Feb. 8, 2018. The entire contents of each of the prior applications are incorporated by reference herein.

FIELD OF THE INVENTION

The present disclosure relates to a crystal form of 3,4-dihydrothieno[3,2-d]pyrimidine compound, a preparation method thereof, and also a use of the crystal form in the preparation of a medicament for the treatment of diseases related to the virus HCMV.

BACKGROUND OF THE INVENTION

Human cytomegalovirus (HCMV) is one of the eight human herpesviruses, with a worldwide distribution and high clinical findings, Despite the advances in diagnosis and treatment, human cytomegalovirus infection still has significant complications during pregnancy and under the clinical conditions associated with hypoimmunity, such as organ or bone marrow transplantation, cancer and AIDS. Currently approved antiviral drugs include ganciclovir (GCVO, its prodrug valganciclovir (VGCV), fosearnet sodium (FOS) and cidofovir (CDV), which are inhibitors targeting the DNA polymerases of the virus. Although effective, these drugs are limited due to severe toxic side effects, low oral bioavailability (except VGCV), and drug resistance. Ganciclovir has limited efficacy against cytomegalovirus and toxicity. Foscarnet sodium and cidofovir are the two most common alternatives, but both of them are nephrotoxic. Mutations of the viral DNA polymerase targeted by these agents may lead to drug resistance. Therefore, there are still greatly unmet clinical needs in the clinical practice, and we urgently need novel and safer anti-human cytomegalovirus drugs.

SUMMARY OF THE INVENTION

The present disclosure provides a crystal form A of compound 1, wherein the X-ray powder diffraction pattern thereof has characteristic diffraction peaks at the following 2θ angles: 17.69±0.2°, 20.00±0.2°, and 20.63±0.2°.

Compound 1

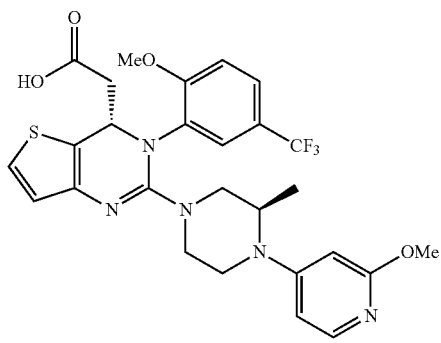

In some embodiments of the present disclosure, provided herein is the crystal form A of compound 1, wherein the X-ray powder diffraction pattern thereof has characteristic diffraction peaks at the following 2θ angles: 9.15±0.2°, 11.06±0.2°, 11.95±0.2°, 17.69±0.2°, 19.03±0.2°, 19.46±0.2°, 20.00±0.2°, and 20.63±0.2°.

In some embodiments of the present disclosure, provided herein is the crystal form A of compound 1, wherein the XRPD pattern thereof is shown in FIG. 1.

In some embodiments of the present disclosure, provided herein is the crystal form A of compound 1, wherein the analytical data of the XRPD pattern thereof is shown in Table 1.

TABLE 1

Analytical data of the XRPD pattern of the crystal form A of compound 1

| | 2θ | d(Å) | Background | Peak height | Peak height % | Area | Area % | Full width at half maximum |
|---|---|---|---|---|---|---|---|---|
| 1 | 9.15 | 9.657 | 206 | 799 | 37.7 | 7076 | 28.8 | 0.148 |
| 2 | 10.327 | 8.5592 | 194 | 150 | 7.1 | 1295 | 5.3 | 0.145 |
| 3 | 11.061 | 7.9923 | 179 | 641 | 30.3 | 5819 | 23.7 | 0.152 |
| 4 | 11.952 | 7.3987 | 174 | 536 | 25.3 | 6262 | 25.5 | 0.196 |
| 5 | 12.188 | 7.2559 | 172 | 334 | 15.8 | 4122 | 16.8 | 0.207 |
| 6 | 13.081 | 6.7623 | 165 | 86 | 4.1 | 865 | 3.5 | 0.169 |
| 7 | 14.355 | 6.1648 | 164 | 417 | 19.7 | 3603 | 14.7 | 0.145 |
| 8 | 15.284 | 5.7923 | 164 | 72 | 3.4 | 888 | 3.6 | 0.207 |
| 9 | 15.972 | 5.5442 | 161 | 335 | 15.8 | 3297 | 13.4 | 0.165 |
| 10 | 17.687 | 5.0104 | 179 | 1240 | 58.5 | 18975 | 77.3 | 0.257 |
| 11 | 18.492 | 4.7941 | 185 | 100 | 4.7 | 983 | 4 | 0.165 |
| 12 | 19.031 | 4.6595 | 210 | 503 | 23.7 | 4482 | 18.3 | 0.149 |
| 13 | 19.464 | 4.5569 | 215 | 922 | 43.5 | 7869 | 32.1 | 0.143 |
| 14 | 19.996 | 4.4367 | 227 | 997 | 47.1 | 8550 | 34.8 | 0.144 |
| 15 | 20.626 | 4.3027 | 203 | 2119 | 100 | 24546 | 100 | 0.194 |
| 16 | 21.512 | 4.1275 | 176 | 113 | 5.3 | 1085 | 4.4 | 0.161 |
| 17 | 22.502 | 3.948 | 164 | 289 | 13.6 | 4048 | 16.5 | 0.235 |
| 18 | 23.092 | 3.8485 | 176 | 259 | 12.2 | 2535 | 10.3 | 0.164 |
| 19 | 23.979 | 3.708 | 162 | 392 | 18.5 | 5433 | 22.1 | 0.232 |
| 20 | 25.535 | 3.4855 | 150 | 107 | 5 | 907 | 3.7 | 0.142 |
| 21 | 26.109 | 3.4101 | 131 | 181 | 8.5 | 3511 | 14.3 | 0.325 |

TABLE 1-continued

Analytical data of the XRPD pattern of the crystal form A of compound 1

| | 2θ | d(Å) | Background | Peak height | Peak height % | Area | Area % | Full width at half maximum |
|---|---|---|---|---|---|---|---|---|
| 22 | 27.669 | 3.2213 | 118 | 227 | 10.7 | 3412 | 13.9 | 0.252 |
| 23 | 28.891 | 3.0878 | 121 | 203 | 9.6 | 1845 | 7.5 | 0.152 |
| 24 | 29.444 | 3.0311 | 117 | 95 | 4.5 | 1817 | 7.4 | 0.321 |
| 25 | 30.825 | 2.8984 | 101 | 134 | 6.3 | 2466 | 10 | 0.309 |
| 26 | 32.106 | 2.7856 | 86 | 98 | 4.6 | 2314 | 9.4 | 0.396 |
| 27 | 35.74 | 2.5102 | 75 | 74 | 3.5 | 1595 | 6.5 | 0.361 |

In some embodiments of the present disclosure, provided herein is the crystal form A of compound 1, wherein the differential scanning calorimetry curve thereof has a starting point of the endothermic peak at 214.47±2° C.

In some embodiments of the present disclosure, provided herein is the crystal form A of compound 1, wherein the DSC curve thereof is shown in FIG. 2.

In some embodiments of the present disclosure, provided herein is the crystal form A of compound 1, wherein the thermogravimetric analysis (TGA) curve thereof has a weight loss of 0.1206% at up to 120.00±2° C.

In some embodiments of the present disclosure, provided herein is the crystal form A of compound 1, wherein the TGA curve thereof is shown in FIG. 3.

The present disclosure also provides a method of preparing the crystal form A, comprising adding the compound 1 to a mixed solvent of alcoholic solvent and water, heating to dissolve, and then cooling and crystallizing.

In some embodiments of the present disclosure, provided herein is the method of preparing the crystal form A, wherein the alcoholic solvent is selected from the group consisting of methanol, ethanol and isopropanol.

In some embodiments of the present disclosure, provided herein is the method of preparing the crystal form A, wherein the mixed solvent of alcoholic solvent and water is a mixed solvent of ethanol and water.

In some embodiments of the present disclosure, provided herein is the method of preparing the crystal form A, wherein in the mixed solvent of alcoholic solvent and water, the volume ratio of the alcoholic solvent to water is selected from 1:0.2 to 1:1.5.

The present disclosure also provides a use of the crystal form A of compound 1 in the preparation of an anti-HCMV medicament.

Technical Effects

The crystal form A of compound 1 has stable properties, low hygroscopicity, and good prospect of druggability.

Compound 1 shows good inhibitory activity against the replication of human cytomegalovirus in vitro.

Compound 1 has a reasonable plasma protein binding rate in the plasma of three species, indicating that in the plasma of the above three species, the test compound has a moderate ratio of the free drug concentration, and a good druggability.

Compound 1 shows good efficacy in vivo. During the in vivo assay of pharmacodynamic study, body weights of the mice were stable, and no abnormality was found in the clinical observations, indicating that this—compounds has no significant side effects on mice at the administered dose.

Compound 1 is mainly used to prevent human cytomegalovirus infection in patients undergoing allogeneic hematopoietic stem cell transplantation, kidney transplantation, lung transplantation and pancreas transplantation. Compared with the existing clinical drugs, it has less toxic side effects, better oral bioavailability, and lower risk of drug resistance.

Definition and Description

Unless otherwise stated, the following terms and phrases used herein are intended to have the following meanings. A specific phrase or term should not be considered uncertain or unclear without a specific definition, but should be understood in the ordinary sense. When a trade name appears herein, it is intended to refer to the corresponding commodity or the active ingredient thereof.

The intermediate compounds of the present disclosure can be prepared by a variety of synthesis methods well known to those skilled in the art, including the specific embodiments listed below, the embodiments formed by combining them with other chemical synthesis methods, and the equivalent alternative methods well known to those skilled in the art. The preferred embodiments include, but are not limited to, the examples of the present disclosure.

The chemical reactions in the specific embodiments disclosed herein are completed in a suitable solvent, which must be suitable for the chemical changes of the present disclosure and the reagents and materials required. In order to obtain the compound of the present disclosure, it is sometimes necessary for those skilled in the art to modify or select synthesis steps or reaction schemes based on the existing embodiments.

The present disclosure will be described in detail below through examples, which are not intended to limit the present disclosure.

All solvents used in the present disclosure are commercially available and can be used without further purification.

The present disclosure uses the following abbreviations: DMF stands for dimethylformamide; MsOH stands for methanesulfonic acid; EtOH stands for ethanol; NaOH stands for sodium hydroxide; M stands for mol/L; and NBS stands for N-bromosuccinimide.

The compounds are named manually or ChemDraw® software, and the commercially available compounds use the supplier catalog names.

X-Ray Powder Diffraction (XRPD) Method Used in the Present Disclosure

Instrument model: Bruker D8 advance X-ray diffractometer

Testing method: about 10 to 20 mg of sample was used for XRPD analysis.

The detailed XRPD parameters were as follows:
Light tube: Cu, kα, (λ=1.54056 Å).
Voltage of the light tube: 40 kV, current of the light tube: 40 mA
Divergence slit: 0.60 mm
Detector slit: 10.50 mm
Anti-scatter slit: 7.10 mm
Scanning range: 4 to 40 deg
Step size: 0.02 deg
Step length: 0.12 seconds
Rotation speed of sample disk: 15 rpm Differential Scanning Calorimetry (DSC) Method Used in the Present Disclosure
Instrument model: TA Q2000 differential scanning calorimeter
Testing method: the sample (about 1 mg) was taken and put in the DSC aluminum pan for testing. Under the condition of 50 mL/min $N_2$, the sample was heated from 30° C. to 280° C. at a heating rate of 10° C./min Thermogravimetric Analysis (TGA) Method Used in the Present Disclosure
Instrument model: TA Q5000IR thermogravimetric analyzer
Testing method: the sample (2 to 5 mg) was taken and put into a TGA platinum pot for testing. Under the condition of 25 mL/min $N_2$, the sample was heated from room temperature to 300° C. at a heating rate of 10° C./min

BRIEF DESCRIPTION OF THE DRAWINGS

Figure 3:
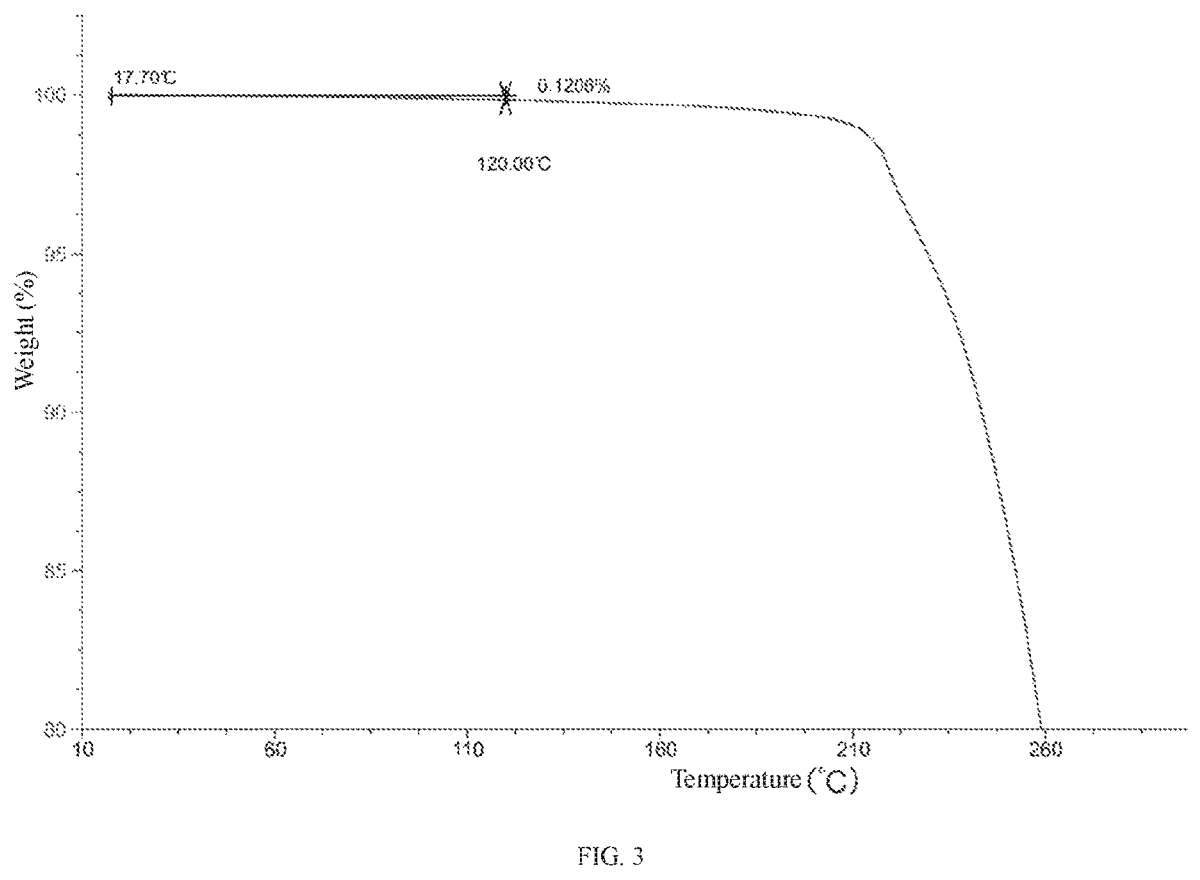

FIG. 3 is the TGA curve of the crystal form A of compound 1.

DETAILED DESCRIPTION OF THE INVENTION

Figure 1:
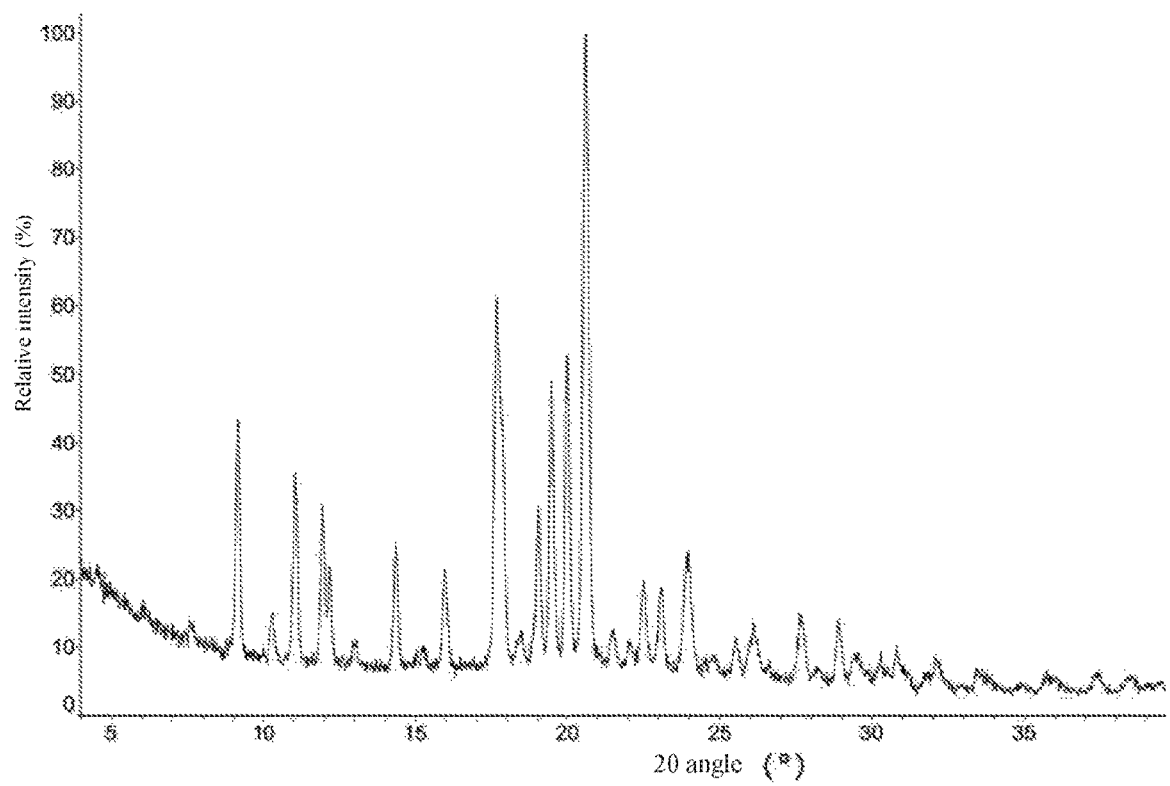
FIG. 1 is the XRPD pattern of the crystal form A of compound 1 using Cu-Kα radiation.

In order to better understand the content of the present disclosure, the present disclosure is further illustrated below in conjunction with specific examples, but the specific embodiments are not intended to limit the content of the present disclosure.

Reference Example 1: Preparation of Compound BB-1

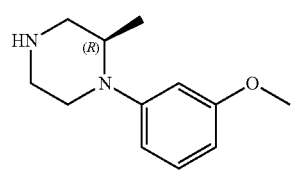

BB-1

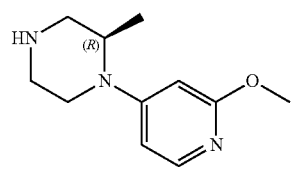

BB-1

The synthetic route was as follows:

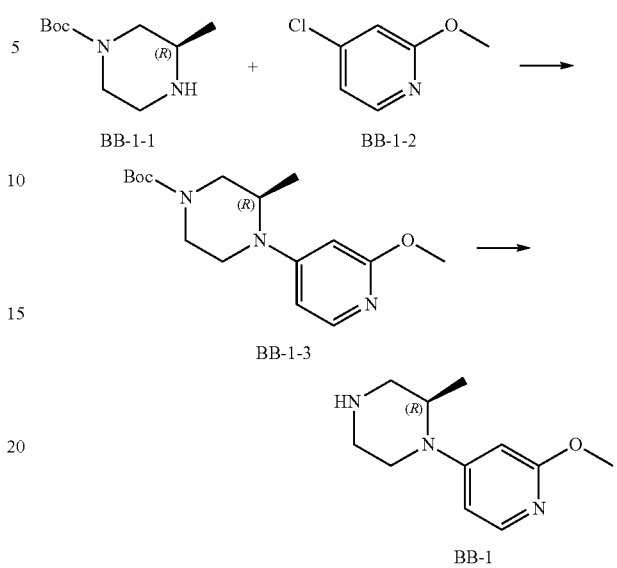

Step 1: Synthesis of Compound BB-1-3

At room temperature, tri-tert-butylphosphine (1 M toluene solution, 0.01 eq), $Pd_2(dba)_3$ (91.48 mg, 0.01 eq) and potassium tert-butoxide (1.68 g, 1.50 eq) were added to a solution of compound BB-1-1 (2.00 g, 1.00 eq) and compound BB-1-2 (1.51 g, 1.05 eq) in toluene (40.00 mL). The reaction solution was stirred at 100° C. for 12 hours under the protection of nitrogen. The compound was concentrated to dryness with a rotary evaporator, and the crude product was purified by silica gel column chromatography (PE/EtOAc=3/1) to give the compound BB-1-3 (2.30 g).

Step 2: Synthesis of Compound BB-1

Trifluoroacetic acid (4.62 g, 6.91 eq) was added to a solution of BB-1-3 (1.80 g, 1.00 eq) in dichloromethane (30.00 mL), and the reaction solution was stirred at 15° C. for 12 hours. The reaction solution was concentrated to dryness with a rotary evaporator to give a crude product of compound BB-1 (4.5 g, TFA). MS (ESI)m/z: 208.0 [M+1].

Example 1: Preparation of Compound 1

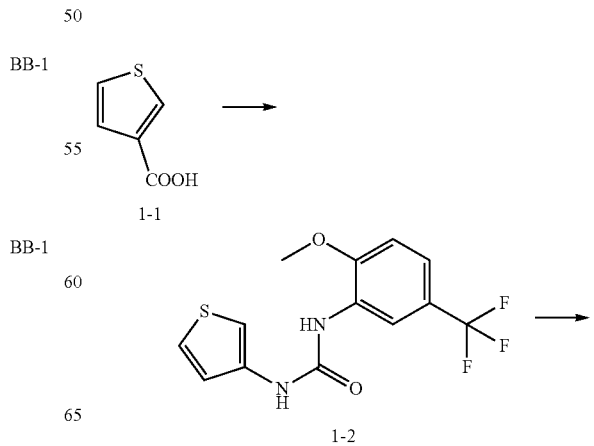

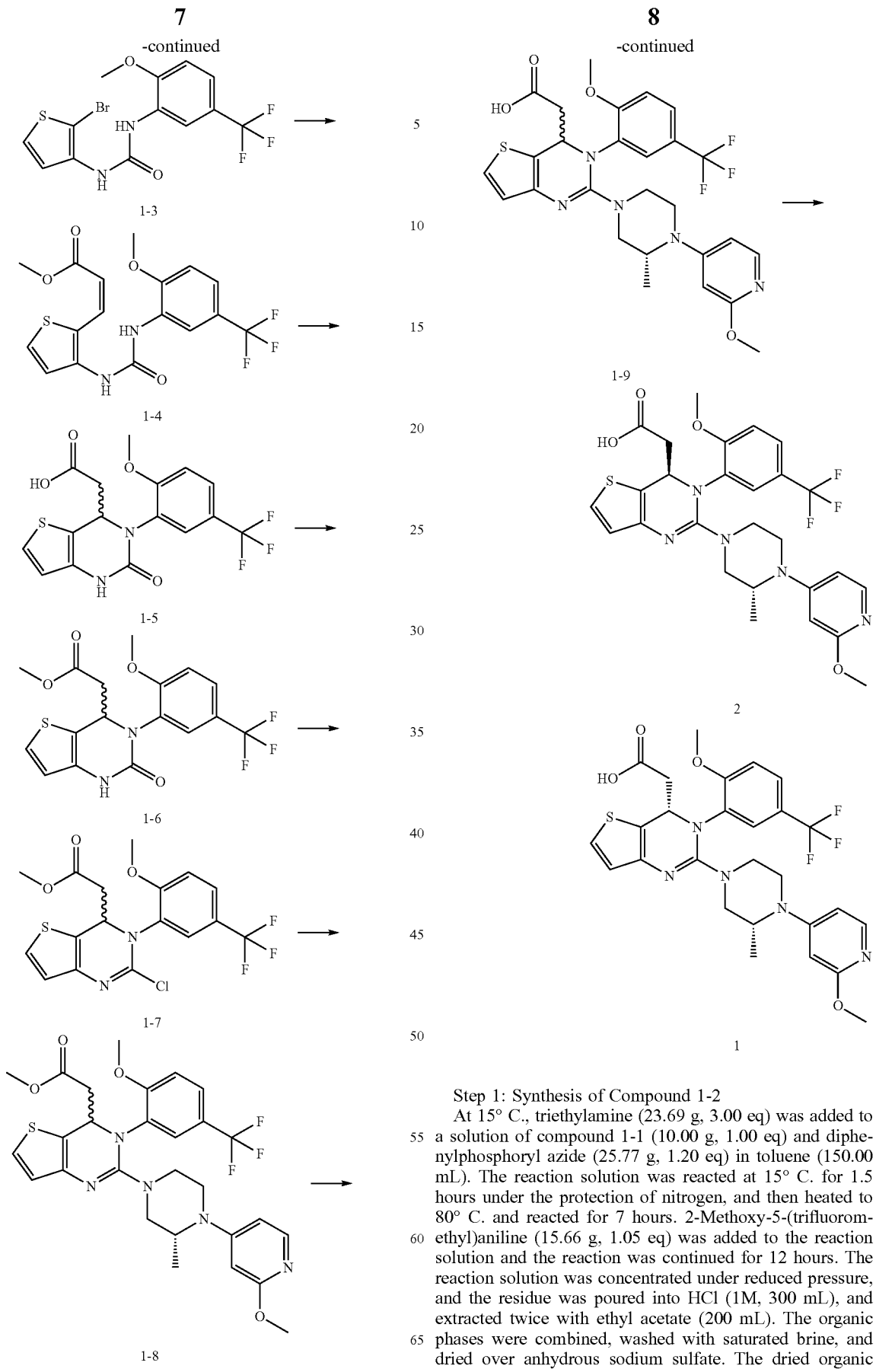

Step 1: Synthesis of Compound 1-2

At 15° C., triethylamine (23.69 g, 3.00 eq) was added to a solution of compound 1-1 (10.00 g, 1.00 eq) and diphenylphosphoryl azide (25.77 g, 1.20 eq) in toluene (150.00 mL). The reaction solution was reacted at 15° C. for 1.5 hours under the protection of nitrogen, and then heated to 80° C. and reacted for 7 hours. 2-Methoxy-5-(trifluoromethyl)aniline (15.66 g, 1.05 eq) was added to the reaction solution and the reaction was continued for 12 hours. The reaction solution was concentrated under reduced pressure, and the residue was poured into HCl (1M, 300 mL), and extracted twice with ethyl acetate (200 mL). The organic phases were combined, washed with saturated brine, and dried over anhydrous sodium sulfate. The dried organic phase was concentrated under reduced pressure, and the residue was washed with PE:EtOAc (2:1) to give the compound 1-2 (10.00 g, 24.41 mmol, yield: 31.28%). $^1$H NMR (400 MHz, DMSO-d6) 9.72 (s, 1H), 8.58 (s, 1H), 8.47 (s, 1H), 7.47-7.48 (m, 1H), 7.33-7.35 (m, 2H), 7.20 (d, J=8.4 Hz, 2H), 7.02 (d, J=5.2 Hz, 1H), 3.92 (s, 3H).

Step 2: Synthesis of Compound 1-3

At 0° C., compound NBS (5.63 g, 1.00 eq) was added to a solution of compound 1-2 (10.00 g, 1.00 eq) in dichloromethane (150.00 mL), and the resulting mixture was stirred at 0° C. for 2 hours. The reaction solution was filtered, and the filter cake was dried to give the compound 1-3 (6.80 g, yield: 46.80%). MS (ESI)m/z: 397.0 [M+1].

Step 3: Synthesis of Compound 1-4

At room temperature, compound Pd(dppf)Cl$_2$ (1.26 g, 0.10 eq) and potassium carbonate (7.14 g, 3.00 eq) were added to a solution of compound 1-3 (6.80 g, 1.00 eq) and (E)-methyl 3-(4,4,5,5-tetramethyl-1,3,2-dioxaborolan-2-yl) acrylate (7.30 g, 2.00 eq) in tetrahydrofuran (80.00 mL) and water (10.00 mL). The resulting mixture was stirred at 55° C. for 12 hours under the protection of nitrogen. The reaction solution was evaporated to dryness with a rotary evaporator, and purified by column chromatography (PE/EtOAc=5/1) to give the compound 1-4 (2.60 g, 4.68 mmol, yield: 27.17%). MS (ESI)m/z: 401.1 [M+1].

Step 4: Synthesis of Compound 1-5

At room temperature, a solution of lithium hydroxide in water (1 M, 6.62 mL, 1.00 eq) was added to a solution of compound 1-4 (2.65 g, 1.00 eq) in tetrahydrofuran (15.00 mL). The resulting mixture was stirred at 40° C. for 12 hours, and then evaporated to dryness with a rotary evaporator to give a crude product of compound 1-5 (2.80 g).

Step 5: Synthesis of Compound 1-6

At 0° C., thionyl chloride (2.40 g, 3.00 eq) was added to a solution of compound 1-5 (6.80 g, 1.00 eq) in methanol (60.00 mL). The resulting mixture was stirred at 70° C. for 3 hours under the protection of nitrogen. The reaction solution was evaporated to dryness with a rotary evaporator, and purified by column chromatography (PE/EtOAc=3/1 to 3/2) to give the compound 1-6 (800.00 mg, 1.58 mmol, yield: 23.54%). $^1$H NMR: (400 MHz, CDCl$_3$) 7.59 (d, J=7.2 Hz, 1H), 7.16 (d, J=5.2 Hz, 1H), 7.05 (d, J=8.8 Hz, 1H), 6.57 (d, J=5.2 Hz, 1H), 5.40-5.43 (m, 1H), 3.89 (s, 3H), 3.57 (s, 3H), 2.75-2.81 (m, 2H).

Step 6: Synthesis of Compound 1-7

At room temperature, compound 1-6 (350 mg, 1.00 eq) was dissolved in phosphorus oxychloride (17.13 g) and the resulting mixture was stirred at 110° C. for 12 hours under the protection of nitrogen. N,N-diisopropylethylamine (564.90 mg, 5.00 eq) was added to the reaction solution and further stirred at 110° C. for 3 hours under the protection of nitrogen. The reaction solution was concentrated under reduced pressure, and the residue was added to water (100 mL). The resulting mixture was adjusted to neutrality with sodium bicarbonate, and extracted three times with ethyl acetate (80 mL). The organic phases were combined, washed with saturated brine, and dried over anhydrous sodium sulfate. The dried organic phase was filtered, and the filtrate was concentrated under reduced pressure to give a crude product of compound 1-7 (300.00 mg). MS (ESI)m/z: 419.1 [M+1].

Step 7: Synthesis of Compound 1-8

At room temperature, potassium carbonate (495 mg, 10.00 eq) was added to a solution of compound 1-7 (150.00 mg, 1.00 eq) and BB-1 (172.61 mg, 1.50 eq, TFA) in acetonitrile (5.00 mL). The resulting mixture was stirred at 80° C. for 12 hours. The reaction solution was filtered, and the filtrate was concentrated to dryness under reduced pressure to give a crude product of compound 1-8 (250.00 mg). MS (ESI)m/z: 590.2 [M+1].

Step 8: Synthesis of Compound 1-9

At room temperature, sodium hydroxide (122.40 mg, 3.00 eq) was added to a solution of compound 1-8 (600.00 mg, 1.00 eq) in methanol (3.00 mL), tetrahydrofuran (3.00 mL) and water (1.00 mL), and the resulting mixture was stirred at 15° C. for 3 hours. The reaction solution was evaporated to dryness with a rotary evaporator, and the residue was purified by HPLC to give the compound 1-9 (450.00 mg, yield: 76.65%). MS (ESI)m/z: 576.1 [M+1].

Step 9: Synthesis of Compounds 1 and 2

Compound 1-9 (450.00 mg, 1.00 eq) was subjected to SFC preparation method (Column type (IC (250 mm×30 mm, 10 μm)), mobile phase (A: carbon dioxide, B: methanol containing 0.1% ammonia, gradient: B 40%-40%)) to give the compound 1 (130.00 mg, yield: 28.46%, retention time: the first peak) and the compound 2 (150.00 mg, yield: 32.40%, retention time: the second peak).

Compound 1 $^1$H NMR (400 MHz, d$_4$-MeOH) δ 7.75 (br. s., 1H), 7.55 (d, J=8.0 Hz, 1H), 7.12-7.38 (m, 2H), 6.98 (d, J=5.0 Hz, 1H), 6.51 (br. s., 1H), 6.10 (br. s., 1H), 5.05 (br. s., 1H), 4.10 (br. s., 1H), 3.84 (s, 6H), 3.63-3.72 (m, 2H), 3.14-3.29 (m, 1H), 2.78-3.11 (m, 3H), 2.52-2.72 (m, 1H), 0.50 (br. s., 3H), MS (ESI)m/z: 576.1 [M+1].

Compound 2 $^1$H NMR (400 MHz, d$_4$-MeOH) δ 7.76 (d, J=5.8 Hz, 1H), 7.62 (d, J=8.5 Hz, 1H), 7.14-7.41 (m, 2H), 6.98 (d, J=5.3 Hz, 1H), 6.43 (d, J=5.3 Hz, 1H), 6.01 (br. s., 1H), 5.15 (br. s., 1H), 3.96 (br. s., 1H), 3.63-3.87 (m, 6H), 3.54 (br. s., 1H), 2.82-3.12 (m, 2H), 2.63 (dd, J=7.3, 14.6 Hz, 1H), 1.00-1.12 (m, 3H). MS (ESI)m/z: 576.1 [M+1].

Example 2: Preparation of Crystal Form A

Compound 1 (50 mg) was added to a mixed solvent (ethanol:water=1:1, 1 mL), and stirred at 25° C. and 700 rpm for 36 hours. The resulting suspension was centrifuged. The solid was dried in vacuum at 35° C. for 12 hours to give the crystal form A.

Assay Example 1

Fluorescence Decay Assay Against Human Cytomegalovirus

The antiviral activity of the compound against human cytomegalovirus (HCMV) was evaluated by determining the median effective concentration ($EC_{50}$) value of the compound. The HCMV used in this assay was inserted with enhanced green fluorescent protein (EGFP) as a reporter gene by gene recombination, and thus the replication of the virus in cells can be reflected by the expression level of GFP. The inhibitory activity of the compound on the expression of GFP in HCMV was evaluated by determining the fluorescence intensity in the wells of different concentrations of the compound using a high-content cell analysis platform Acumen eX3.

Fluorescence Decay Assay Against HCMV

MRCS cells were inoculated into a black 96-well cell culture plate at a density of 20,000 cells per well, and then incubated overnight in a 37° C., 5% $CO_2$ incubator. US3-6-EGFP-HCMV-AD169 viruses were added to the cell culture wells at a certain MOI (0.003 to 0.1), and incubated in a 37° C., 5% $CO_2$ incubator for 3 hours. After adsorption of viruses, the medium containing viruses was pipetted out, and 200 μl of cell culture medium containing different concentrations of the compound (4-fold dilution, 6 test concentrations) was added. The final concentration of DMSO in the medium was 1%. Virus control wells (DMSO was added, without compound) and inhibition control wells (high concentration of control compound was added) were set. The cell plate was incubated in a 37° C., 5% $CO_2$ incubator for 10 days, and the liquid was renewed on the $4^{th}$ and $7^{th}$ days. After 10 days of culture, the fluorescence intensity was detected with a high content cell analysis platform Acumen eX3 (TTP LabTech). The original data was used to calculate the antiviral activity of the compound.

$$\text{Inhibition \%} = 100 - \frac{\text{Signal value of compound well} - \text{Average signal value of inhibition control well}}{\text{Average signal value of virus control well} - \text{Average signal value of inhibition control well}} \times 100$$

The inhibition percentages were imported into the GraphPad Prism software respectively for data processing to obtain a corresponding dose-response curve for the compound, and $EC_{50}$ value of the test compound was obtained.

The result is shown in Table 2:

TABLE 2

| Compound | $EC_{50}$ (μM) |
|---|---|
| Compound 1 | 0.0002 |

Conclusion: Compound 1 shows good inhibitory activity against the replication of human cytomegalovirus in vitro.

Assay Example 2

Determination of the Plasma Protein Binding Rate of the Compound

The protein-binding rates of the test compound in the plasma of CD-1 mice, SD rats and human were evaluated by the equilibrium dialysis method. Compound 1 was diluted into the plasma of the above three species respectively to prepare samples with a final concentration of 2 μM. The samples were then added to a 96-well equilibrium dialysis device, and dialyzed against phosphate buffer solution at 37° C. for 4 hours. Warfarin was used as a control compound in the assay. The concentrations of the test compound and warfarin in the plasma and buffer were determined by LC-MS/MS method.

The results are shown in Table 3.

TABLE 3

| Compound No. | Plasma Protein Binding PPB bound(%) |
|---|---|
| Compound 1 | 94.0(H), 93.9(R), 98.3(M) |

Note:
H stands for human, R stands for rat, and M stands for mouse.

Conclusion: Compound 1 has a reasonable plasma protein binding rate in the plasma of the three species, indicating that in the plasma of the above three species, the test compound has a moderate ratio of the free drug concentration, and a good druggability.

Assay Example 3

Human Cytomegalovirus (HCMV) Transplantation Model in Mice

Gelatin sponge containing HCMV was transplanted into mice. After 9 days of continuous administration, the gelatin sponge was collected for plaque detection. The anti-HCMV effect of the compound in this model was evaluated by detecting the amount of HCMV in the gelatin sponge.

The animals used in the assay were NOD SCID mice (purchased from Shanghai SLAC Laboratory Animal Co., Ltd.), 5 weeks old, and male. There were 5 animals in each group. The day on which the mice were subjected to gelatin sponge transplantation was set as day 0. Human foreskin fibroblasts (HFF, MOI=0.03) were infected with HCMV (strain: GFP-AD169) in advance, and then the HFF cells infected with HCMV were added to 1 $cm^2$ gelatin sponges and incubated for use. The animals were anesthetized by intraperitoneal injection of pentobarbital sodium at a dose of 75 mg/kg (10 ml/kg). After the animals entered the deep anesthesia state, the treated gelatin sponges were subcutaneously transplanted into the back of the mice. From day 1 to day 9, 8 mg/kg (10 ml/kg) of compound 1 was administered orally once per day. On the day 9, four hours after the administration, the gelatin sponges were taken out and digested, and then the plaques were detected. The assay data showed that compound 1 exhibited a decrease in HCMV viral load of 2.38 log PFU/ml, demonstrating excellent drug efficacy in vivo. During the assay of pharmacodynamic study in vivo, body weights of the mice were stable, and no abnormality was found in the clinical observations, indicating that this compounds has no obvious side effects on mice at the administered dose.

What is claimed is:

1. A crystal form A of compound 1, wherein the X-ray powder diffraction pattern thereof has characteristic diffraction peaks at the following 2θ angles: 17.69±0.2°, 20.00±0.2°, and 20.63±0.2°, Compound 1

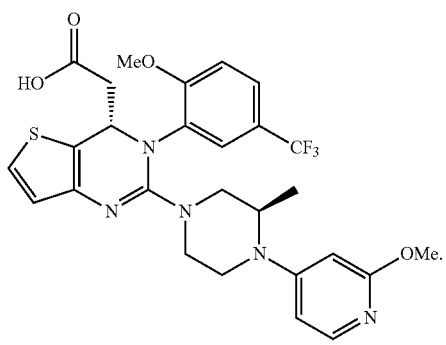

2. The crystal form A of compound 1 according to claim 1, wherein the X-ray powder diffraction pattern thereof has characteristic diffraction peaks at the following 2θ angles: 9.15±0.2°, 11.06±0.2°, 11.95±0.2°, 17.69±0.2°, 19.03±0.2°, 19.46±0.2°, 20.00±0.2°, and 20.63±0.2°.

3. The crystal form A of compound 1 according to claim 2, wherein the XRPD pattern thereof is shown in FIG. 1.

4. The crystal form A of compound 1 according to claim 1 wherein the differential scanning calorimetry curve thereof has a starting point of the endothermic peak at 214.47±° C.

Figure 2:
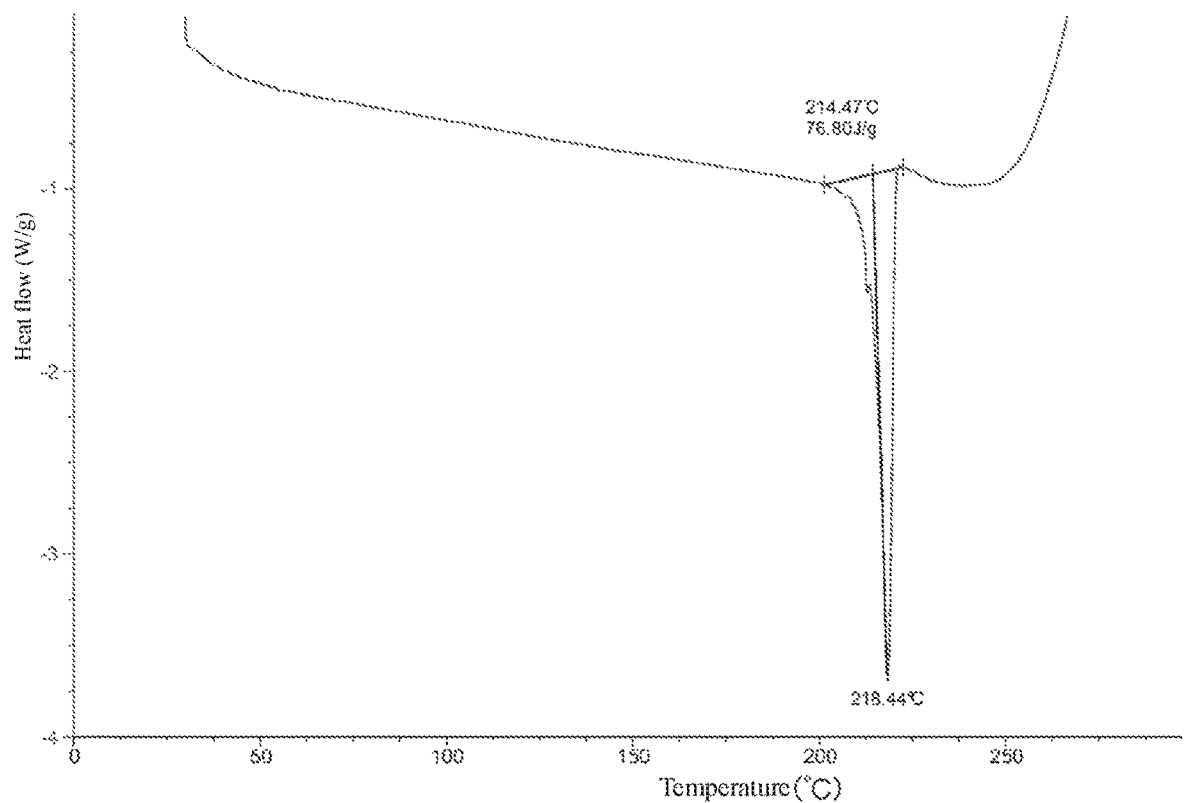
FIG. 2 is the DSC curve of the crystal form A of compound 1.

5. The crystal form A of compound 1 according to claim 4, wherein the DSC curve thereof is shown in FIG. 2.

6. The crystal form A of compound 1 according to claim 1 wherein the thermogravimetric analysis curve thereof has a weight loss of 0.1206% at 120.00±2° C.

7. The crystal form A of compound 1 according to claim 6, wherein the TGA curve thereof is shown in FIG. 3.

8. A method of preparing the crystal form A of compound 1,

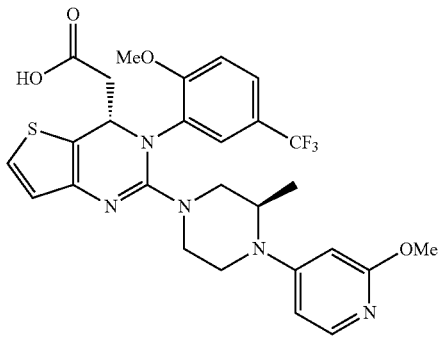

Compound 1 comprising adding the compound 1 to a mixed solvent of alcoholic solvent and water, heating to dissolve, and then cooling and crystallizing.

9. The method of preparing the crystal form A of compound 1 according to claim 8, wherein the alcoholic solvent is selected from the group consisting of methanol, ethanol and isopropanol.

10. The method of preparing the crystal form A of compound 1 according to claim 8, wherein the mixed solvent of alcoholic solvent and water is a mixed solvent of ethanol and water.

11. The method of preparing the crystal form A of compound 1 according to claim 8, wherein in the mixed solvent of alcoholic solvent and water, the volume ratio of the alcoholic solvent to water is selected from 1:0.2 to 1:1.5.

12. A method of treating a disease related to HCMV virus in a subject in need thereof, comprising administering to the subject the crystal form A of compound 1 according to claim 1.

13. The crystal form A of compound 1 according to claim 4, wherein the thermogravimetric analysis curve thereof has a weight loss of 0.1206% at 120.00±2° C.

14. The crystal form A of compound 1 according to claim 7, wherein the TGA curve thereof is shown in FIG. 3.

* * * * *

UNITED STATES PATENT AND TRADEMARK OFFICE
CERTIFICATE OF CORRECTION

PATENT NO. : 11,174,270 B2
APPLICATION NO. : 16/968206
DATED : November 16, 2021
INVENTOR(S) : Jian Xiong et al.

Page 1 of 1

It is certified that error appears in the above-identified patent and that said Letters Patent is hereby corrected as shown below:

In the Claims

Column 12, Lines 65-67, should read:
4. The crystal form A of compound 1 according to any one of claims 1, wherein the differential scanning calorimetry curve thereof has a starting point of the endothermic peak at 214.47 ±2° C.

Signed and Sealed this
Eighth Day of October, 2024

Katherine Kelly Vidal
*Director of the United States Patent and Trademark Office*